(12) United States Patent
Hanson et al.

(10) Patent No.: US 10,561,442 B2
(45) Date of Patent: Feb. 18, 2020

(54) NAVIGATION INSTRUMENTS FOR SUBCHONDRAL BONE TREATMENT

(71) Applicant: ZIMMER KNEE CREATIONS, INC., Exton, PA (US)

(72) Inventors: Shaun B. Hanson, West Chester, PA (US); Christopher D. Mandeen, West Chester, PA (US); Peter F. Sharkey, Villanova, PA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 353 days.

(21) Appl. No.: 15/527,449

(22) PCT Filed: Nov. 24, 2015

(86) PCT No.: PCT/US2015/062404
§ 371 (c)(1),
(2) Date: May 17, 2017

(87) PCT Pub. No.: WO2016/085973
PCT Pub. Date: Jun. 2, 2016

(65) Prior Publication Data
US 2017/0360473 A1 Dec. 21, 2017

Related U.S. Application Data

(60) Provisional application No. 62/083,456, filed on Nov. 24, 2014.

(51) Int. Cl.
*A61B 17/58* (2006.01)
*A61B 17/60* (2006.01)
(Continued)

(52) U.S. Cl.
CPC ...... *A61B 17/3403* (2013.01); *A61B 17/3472* (2013.01); *A61B 17/8816* (2013.01);
(Continued)

(58) Field of Classification Search
CPC combination set(s) only.
See application file for complete search history.

(56) References Cited

U.S. PATENT DOCUMENTS

2014/0074117 A1* 3/2014 Hanson .............. A61M 5/3287
606/130

FOREIGN PATENT DOCUMENTS

WO WO-2011063267 A1 5/2011
WO WO-2011063281 A1 5/2011
(Continued)

OTHER PUBLICATIONS

"Application Serial No. PCT/US2015/062404, Invitation to Pay Additional Fees and Partial Search Report dated Feb. 26, 2016", 8 pgs.
(Continued)

*Primary Examiner* — Sameh R Boles
(74) *Attorney, Agent, or Firm* — Schwegman Lundberg & Woessner, P.A.

(57) ABSTRACT

An instrument for navigating to a target area near a subchondral defect of a bone and associated methods are disclosed. The instrument can include a body portion having a patient specific surface defining a negative impression of a portion of a skin surface of a patient, and a targeting device coupled to the body portion, the targeting device including a rail and at least one device portal configured to guide a device into a subchondral region of the bone for treatment at the target area.

13 Claims, 7 Drawing Sheets

(51) Int. Cl.
*A61F 2/00* (2006.01)
*A61B 17/34* (2006.01)
*A61B 90/00* (2016.01)
*A61B 17/88* (2006.01)
*A61B 17/00* (2006.01)

(52) U.S. Cl.
CPC ............... *A61B 2017/00716* (2013.01); *A61B 2017/3407* (2013.01); *A61B 2017/3411* (2013.01); *A61B 2090/3937* (2016.02); *A61B 2090/3954* (2016.02)

(56) References Cited

FOREIGN PATENT DOCUMENTS

| WO | WO-2014053913 A2 | 4/2014 |
|----|------------------|--------|
| WO | WO-2016085973 A1 | 6/2016 |

OTHER PUBLICATIONS

"International Application Serial No. PCT/US2015/062404, International Search Report dated May 10, 2016", 7 pgs.
"International Application Serial No. PCT/US2015/062404, Written Opinion dated May 10, 2016", 7 pgs.
"European Application Serial No. 15805371.6, Response filed Feb. 12, 2018 to Action dated Aug. 2, 2017", 11 pgs.
"European Application Serial No. 15805371.6, Communication Pursuant to Article 94(3) EPC dated Jul. 9, 2018", 4 pgs.
"European Application Serial No. 15805371.6, Response filed Nov. 19, 2018 to Communication Pursuant to Article 94(3) EPC dated Jul. 9, 2018", 25 pgs.

\* cited by examiner

NAVIGATION INSTRUMENTS FOR SUBCHONDRAL BONE TREATMENT

CLAIM OF PRIORITY

This application is a U.S. National Stage Filing under 35 U.S.C. 371 from International Application No. PCT/US2015/062404, filed Nov. 24, 2015, and published as WO 2016/085973 A1, which claims the benefit of U.S. Provisional Patent Application Ser. No. 62/083,456, filed on Nov. 24, 2014, the benefit of priority of each of which is claimed hereby, and each of which are incorporated by reference herein in its entirety.

TECHNICAL FIELD

This patent document pertains generally, but not by way of limitation, to instruments for navigating to a target area near a subchondral defect of a bone and associated methods, and in particular to, instruments that provide controlled delivery of injectable materials into the bone for treatment of the subchondral bone defect.

BACKGROUND

Human joints, in particular the knee, hip, ankle, and spine, are susceptible to degeneration from disease, trauma, and long-term repetitive use that eventually lead to pain. Knee pain, for example, is the impetus for a wide majority of medical treatments and associated medical costs. The most popular theory arising from the medical community is that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, especially in joints such as the knee and ankle, has been found to correlate poorly with the incidence and magnitude of knee pain. Because of this, surgeons and medical practitioners have struggled to deliver consistent, reliable pain relief to patients especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, microfracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore joint function. Both non-surgical and surgical treatments are currently available for joint repair.

Non-surgical treatments include weight loss (for the overweight patient), activity modification (low impact exercise), quadriceps strengthening, patellar taping, analgesic and anti-inflammatory medications, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

Surgical options include arthroscopic partial meniscectomy and loose body removal. Most surgical treatments conventionally employ mechanical fixation devices such as screws, plates, staples, rods, sutures, and the like are commonly used to repair damaged bone. These fixation devices can be implanted at, or around, the damaged region to stabilize or immobilize the weakened area, in order to promote healing and provide support. Injectable or fillable hardening materials such as bone cements, bone void fillers, or bone substitute materials are also commonly used to stabilize bone defects.

High tibial osteotomy (HTO) or total knee arthroplasty (TKA) is often recommended for patients with severe pain associated with osteoarthritis, especially when other non-invasive options have failed. Both procedures have been shown to be effective in treating knee pain associated with osteoarthritis.

However, patients generally only elect HTO or TKA with reluctance. Both HTO and TKA are major surgical interventions and may be associated with severe complications. HTO is a painful procedure that may require a long recovery. TKA patients often also report the replaced knee lacks a "natural feel" and have functional limitations. Moreover, both HTO and TKA have limited durability. Accordingly, it would be desirable to provide a medical procedure that addresses the pain associated with osteoarthritis and provides an alternative to a HTO or TKA procedure.

OVERVIEW

The present inventors recognize, among other things, that an instrument for navigating to a target area near a subchondral defect of a bone by using a patient's anatomical landmarks can be beneficial. The instruments and methods of the present disclosure can improve accuracy of injecting the bone with a bone void filler and eliminate or reduce the need for fluoroscopy assistance during surgery to inject the bone void filler.

To further illustrate the instrument and method for navigating to a target area system disclosed herein, a non-limiting list of examples is provided here:

In Example 1, an instrument for navigating to a target area near a subchondral defect of a bone, includes a body portion having a front surface and a patient specific surface opposite the front surface, the patient specific surface defining a negative impression of a portion of a skin surface of a patient, and a targeting device configured to be attached to the front surface of the body portion, the targeting device including a rail and at least one device portal configured to guide a device into a subchondral region of the bone for treatment at the target area.

In Example 2, Example 1 is optionally configured such that the negative impression includes an imprint of at least one anatomical landmark.

In Example 3, Examples 1 or 2 are optionally configured such that the at least one anatomical landmark includes first and second anatomical landmarks, wherein the first anatomical landmark is a patella and the second anatomical landmark is a tibial tubercle.

In Example 4, Examples 1 through 3 are optionally configured such that the body portion includes a magnetic resonance image marker.

In Example 5, Examples 1 through 4 are optionally configured such that the targeting device is releasably coupled to the body portion.

In Example 6, Examples 1 through 5 are optionally configured such that the targeting device is non-releasably coupled to the body portion.

In Example 7 Examples 1 through 6 are optionally configured such that the at least one device portal defines a trajectory and is configured to provide accurate and controlled delivery of the device to the target area.

In Example 8, Examples 1 through 7 are optionally configured such that the at least one device portal is provided on the rail for access to the target area.

In Example 9, Examples 1 through 8 are optionally configured such that the at least one device portal is provided on an alignment guide attachable to the rail, the alignment guide being detachable and movable along a length of the rail.

In Example 10, Examples 1 through 9 are optionally configured such that the body portion is formed from at least one of plaster, fiberglass, silicone, epoxy, and polyurethane foam.

In Example 11, an instrument for navigating to a target area near a subchondral defect of a bone includes a body portion having a front surface and a patient specific surface opposite the front surface, the patient specific surface defining a negative impression of a portion of a skin surface of a patient, an attachment block attachable to the front surface of the body portion, and a targeting device, the targeting device including: a rail, an elongate portion extending from the rail, the elongate portion attachable to and moveable relative to the attachment block, and at least one device portal configured to guide a device into a subchondral region of the bone for treatment at the target area.

In Example 12, Examples 11 is optionally configured such that the negative impression includes an imprint of at least one anatomical landmark.

In Example 13, Examples 11 or 12 are optionally configured such that the at least one anatomical landmark includes first and second anatomical landmarks, wherein the first anatomical landmark is a patella and the second anatomical landmark is a tibial tubercle.

In Example 14, Examples 11 through 13 are optionally configured such that the body portion includes a visual marker.

In Example 15, Examples 11 through 14 are optionally configured such that the at least one device portal is provided on the rail for access to the target area.

In Example 16, Examples 11 through 15 are optionally configured such that the at least one device portal is provided on an alignment guide attachable to the rail, the alignment guide being detachable and movable along the length of the rail.

In Example 17 a method of accessing a target area near a defect in a bone includes: positioning a molded cast on a patient, the molded cast having a front surface and a patient specific surface defining a negative impression of a skin surface of the patient, the negative impression including an imprint of at least one anatomical landmark, wherein the molded cast includes a visual marker, selecting, based on a magnetic resonance imaging image identifying the visual marker and the defect, a device portal located on a targeting device to access the target site, and accessing the target site with the device via the selected device portal.

In Example 18, Example 17 is optionally configured such that the at least one anatomical landmark is selected from one of a patella and a tibial tubercle.

In Example 19, Examples 17 or 18 are optionally configured to further include: forming the molded cast on the patient such that the molded cast extends over the skin surface including the at least one anatomical landmark, identifying the defect in the bone of the patient under magnetic resonance imaging (MRI), and coupling, while under MRI, the visual marker to the cast to provide a reference point on the molded cast in relation to the defect of the bone.

In Example 20, Examples 17 through 19 are optionally configured to further include, where forming the molded cast on the patient includes identifying the defect in the bone of the patient under magnetic resonance imaging (MRI), and coupling, while under MRI, the visual marker to the cast to provide a reference point on the molded cast in relation to the defect of the bone.

In Example 21, Examples 17 through 20 are optionally configured such that accessing the target area includes creating an access path to the target area.

In Example 22, Examples 17 through 21 are optionally configured to include injecting an injectable material into the bone via the access path for reinforcing the bone.

In Example 23, an instrument for navigating to a target area near a subchondral defect of a bone includes a reference guide including a first portion and a second portion, the first and second portions moveable with respect to each other, the first portion including a first contact pad configured to be aligned with a first anatomical landmark and the second portion including a second contact pad configured to be aligned with a second anatomical landmark, and a targeting device attachable to the reference guide, the targeting device including a rail and at least one device portal configured to guide a device into a subchondral region of the bone for treatment at the target area.

In Example 24, Example 23 is optionally configured such that the first portion includes a first elongate body extending from the first contact pad.

In Example 25, Example 23 or 24 are optionally configured such that the second portion includes a second elongate body extending from the second contact pad, the second elongate body defining a bore that receives the first elongate body of the first portion.

In Example 26, Examples 23 through 25 are optionally configured such that the at least one device portal includes a plurality of device portals provided on the rail for access to the target area.

In Example 27 Examples 23 through 26 are optionally configured such that the at least one device portal includes a plurality of device portals provided on an alignment guide attachable to the rail, the alignment guide being detachable and movable along the length of the rail.

In Example 28, Examples 23 through 27 are optionally configured such that the targeting device includes a main body extending from the rail and a base portion, the main body and the base portion moveable with respect to each other.

In Example 29, Examples 23 through 28 are optionally configured such that the base portion defines a bore and terminates at a support portion, and wherein the bore receives the main body extending from the rail.

In Example 30, Examples 23 through 29 are optionally configured such that the first contact portion has a contact surface configured to contact the first anatomical landmark and the second contact portion has a contact surface configured to contact the second anatomical landmark.

In Example 31, Examples 23 through 30 are optionally configured such that the first anatomical landmark is a patella and the second anatomical landmark is a tibial tubercle.

In Example 32, an instrument for navigating to a target area near a subchondral defect of a bone includes a reference guide, including: a first portion having a first contact portion coupled to a first molded portion, the first molded portion including a first patient specific surface having a contour substantially matching a first anatomical landmark of a patient, and a second portion including a second contact portion coupled to a second molded portion, the second molded portion including a second patient specific surface having a contour substantially matching a second anatomical landmark of the patient, and a targeting device releasably attachable to the reference guide, the targeting device including: a rail, a main body extending from the rail, and at least one device portal configured to guide a device into a subchondral region of the bone for treatment at the target area.

In Example 33, Example 32 is optionally configured such that the first patient specific surface defines an imprint of the first anatomical landmark and the second patient specific surface defines an imprint of the second anatomical landmark.

In Example 34, Examples 32 or 33 are optionally configured such that the first anatomical landmark is a patella and the second anatomical landmark is a tibial tubercle.

In Example 35, Examples 32 through 34 are optionally configured such that the at least one device portal is provided on the rail for access to the target area.

In Example 36, Examples 32 through 35 are optionally configured such that the at least one device portal is provided on an alignment guide attachable to the rail, the alignment guide being detachable and movable along the length of the rail.

In Example 37 Examples 32 through 36 are optionally configured such that the reference guide has a plurality of visual markers for vertical alignment of the targeting device along the reference guide.

In Example 38, a method of accessing a target area near a defect in a bone includes: positioning a reference guide on a patient, the reference guide including a first portion and a second portion, the first portion including a first contact portion configured to be placed on a first anatomical landmark of the patient and the second portion including a second contact portion configured to be placed on a second anatomical landmark of the patient, wherein the reference guide further includes a plurality of visual markers, determining, based on an MRI image identifying the plurality of visual markers and the defect, a coupling location corresponding to one visual marker of the plurality of visual markers, coupling a target device to the reference guide at the coupling location, the target device having a plurality of device portals configured to guide a device into a subchondral region of the bone for treatment at the target site, and accessing the target site with a device via a selected one of the device portals.

In Example 39, Example 38 is optionally configured such that the target device includes a main body and a rail extending from the main body, at least some of the device portals being provided on the rail for access to the target site.

In Example 40, Examples 38 or 39 are optionally configured to include determining, based on the MRI image, the selected one of the device portals to access the target site.

In Example 41, Examples 38 through 40 are optionally configured such that the target device includes a main body and a rail extending from the main body, and wherein at least some of the device portals are provided on an alignment guide attachable to the rail, the alignment guide being detachable and movable along a length of the rail.

In Example 42, Examples 38 through 41 are optionally configured to include determining, based on the MRI image, a location along the rail to position the alignment guide to access the target site.

In Example 43, Examples 38 through 42 are optionally configured such that the reference guide includes: a first molded portion coupled to the first contact portion, the first molded portion having a first patient specific surface defining a negative impression of the first anatomical landmark, and a second molded portion coupled to the second contact portion, the second molded portion having a second patient specific surface defining a negative impression of the second anatomical landmark.

In Example 44, Examples 38 through 43 are optionally configured to include forming the first molded portion and the second molded portion.

In Example 45, Examples 38 through 44 are optionally configured such that forming the first molded portion and the second molded portion includes applying a moldable material on the patient at the first anatomical landmark, coupling the first contact portion to the moldable material, applying the moldable material on the patient at the second anatomical landmark, coupling the second contact portion to the moldable material, and allowing the moldable material to harden.

In Example 46, Examples 38 through 45 are optionally configured such that accessing the target site includes creating an access path to the target area.

In Example 47 Examples 38 through 46 are optionally configured to include injecting an injectable material into the bone via the access path for reinforcing the bone.

In Example 48, an instrument for navigating to a target area near a subchondral defect of a bone includes a body portion having a front surface and a patient specific surface opposite the front surface, the patient specific surface defining a negative impression of a portion of a skin surface of a patient, the negative impression including an imprint of at least one anatomical landmark of the patient, and at least one device portal having a trajectory, the at least one device portal configured to guide a device into a subchondral region of the bone for treatment at the target area.

In Example 49, Example 48 is optionally configured such that the at least one anatomical landmark includes first and second anatomical landmarks, wherein the first anatomical landmark is a patella and the second anatomical landmark is a tibial tubercle.

In Example 50, Examples 48 or 49 are optionally configured such that the body portion includes a magnetic resonance image marker.

In Example 51, a method for forming a patient specific instrument for navigating to a target area near a subchondral defect of a bone of a patient includes receiving or forming a molded cast having a front surface and a patient specific surface defining a negative impression of a skin surface of the patient, the negative impression including an imprint of at least one anatomical landmark, wherein the molded cast includes a visual marker, forming at least one device portal extending through the molded cast, the at least one device portal having a trajectory configured to provide accurate and controlled delivery of the device to the target area of the patient, wherein the trajectory is based on imaging data of the patient.

In Example 52, Example 51 is optionally configured such that forming the molded cast includes applying a moldable material to a patient cast that corresponds to the skin surface of the patient to form the molded cast, and allowing the moldable material to harden.

In Example 53, Examples 51 or 52 are optionally configured to include coupling the visual marker to the molded case based on imaging data of the patient.

In Example 54, Example 51 and Example 53 are optionally configured such that the imaging data is magnetic resonance imaging data.

In Example 55, the instruments or methods of any one or any combination of Examples 1-5 can optionally be configured such that all elements or options recited are available to use or select from.

These and other examples and features of the present instrument and method for navigating to a target area will be set forth in part in the following Detailed Description. This Overview is intended to provide non-limiting examples of the present subject matter—it is not intended to provide an exclusive or exhaustive explanation. The Detailed Description below is included to provide further information about the present orthopedic device holder system and method.

BRIEF DESCRIPTION OF THE DRAWINGS

In the drawings, like numerals can be used to describe similar elements throughout the several views. Like numerals can be used to represent different views or configurations of similar elements. The drawings illustrate generally, by way of example, but not by way of limitation, various embodiments discussed in the present document.

DETAILED DESCRIPTION

Figure 1:
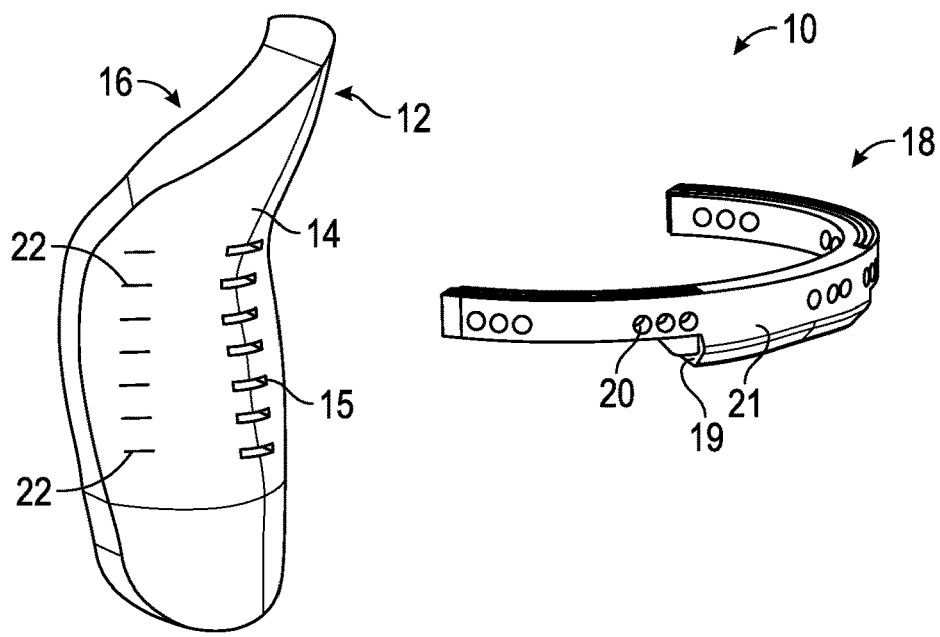
FIG. 1 illustrates an expanded perspective view of an instrument for navigating to a target area near a subchondral defect of a bone, in accordance with at least one example.

Treatment of the bone by mechanical and biological means to restore the normal physiologic stress distribution, and restore the healing balance of the bone tissue at the subchondral level, is a more effective way of treating pain than conventional techniques. That is, treatment can be effectively achieved by mechanically strengthening or stabilizing the defect, and biologically initiating or stimulating a healing response to the defect. This subchondral procedure, and its associated devices, instruments, etc. are also marketed under the registered trademark name of SUBCHONDROPLASTY®. The SUBCHONDROPLASTY® procedure is a response to a desire for an alternative to patients facing partial or total knee replacement.

In general, the SUBCHONDROPLASTY® (also referred to as "SCP®") technique is intended to both strengthen the bone and stimulate the bone. In SCP™, bone fractures or non-unions are stabilized, integrated or healed, which results in reduction of a bone defect, such as a bone marrow lesion or edema. In addition, SCP® restores or alters the distribution of forces in a joint to thereby relieve pain. SCP® can be performed arthroscopically or percutaneously to treat pain by stabilizing chronic stress fracture, resolving any chronic bone marrow lesion or edema, and preserving, as much as possible, the articular surfaces of the joint. SUBCHONDROPLASTY® generally comprises evaluating a joint, for example, by taking an image of the joint, detecting the presence of one or more subchondral defects, diagnosing, which of these subchondral defects is the source of pain, and determining an extent of treatment for the subchondral defect. The technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. Several exemplary treatment modalities for SCP® for the different extents of treatment needed can be employed. Accordingly, a medical practitioner can elect to use the techniques and devices described herein to subchondrally treat any number of bone defects, as he or she deems appropriate.

Detection and identification of the relevant bone marrow lesion or bone marrow edema (BML or BME, respectively) can be achieved by imaging, e.g., magnetic resonance imaging (MRI), X-ray, bone scans, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered can include, among other things, the nature of the defect, size of the defect, location of the defect, etc. For example, bone defects at the edge near the articular surface of periphery of a joint can often be considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP® treatment can be administered on acute stress fractures, BML or BME, or other subchondral defects, as previously mentioned.

The SCP® treatment may continue after surgery. In particular, the patient may be monitored for a change in pain scores, or positive change in function. For example, patients are also checked to see when they are able to perform full weight-bearing activity and when they can return to normal activity. Of note, the SCP® procedure can be revised and thus allows for optional further treatment in the event that a patient requires or desires a joint replacement or other type of procedure. The procedure does not exclude a future joint repair or replacement treatment to be applied, and thus may also be performed in conjunction with other procedures, such as cartilage resurfacing, regeneration or replacement, if desired. In those instances where additional treatment is desired, the SCP® treated area may remain undisturbed while the additional treatment is performed, such as where cartilage resurfacing is desired. Alternatively, the SCP® treated area can be removed, and not create an obstacle to the additional treatment, such as where a partial or total joint replacement is desired. Advantageously, the SCP® treatment may be provided as a first or initial treatment, reserving for the future and possibly forestalling until a later date than otherwise might be the case more invasive treatments such as partial or total joint replacement.

A number of treatment modalities, and associated devices, instruments and related methods of use for performing SUBCHONDROPLASTY® are known. These treatment modalities may be used alone or in combination.

In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In SCP®, the injected material may also serve as a bone stimulator that reinvigorates the desired acute bone healing activity.

For example, polymethylmethacrylate (PMMA) or calcium phosphate (CaP) cement injections can be made at the defect site. PMMA injection can increase the mechanical strength of the bone, allowing it to withstand greater mechanical stresses. CaP cement injection can also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion. Preferably, the injection is made without disrupting the joint surface.

In another treatment modality, the subchondral bone region can be stimulated to trigger or improve the body's natural healing process. For example, in one example of this treatment modality, one or more small holes may be drilled at the region of the defect to increase stimulation (e.g., blood flow, cellular turnover, etc.) and initiate a healing response leading to bone repair. In another example, after holes are drilled an osteogenic, osteoinductive, or osteoconductive agent may be introduced to the site. Bone graft material, for example, may be used to fill the hole. This treatment modality can create a better load-supporting environment leading to long term healing. Electrical or heat stimulation may also be employed to stimulate the healing process of a chronically injured bone. Chemical, biochemical and/or biological stimulation may also be employed in SCP™. For instance, stimulation of bone tissue in SCP® may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. The implant can help create a better load distribution in the subchondral region. In the knees, the implant may support tibio-femoral compressive loads. In addition, the implant can mechanically integrate sclerotic bone with the surrounding healthy bone tissue. The implants can be placed in cancellous bone, through sclerotic bone, or under sclerotic bone at the affected bone region. The implant can also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant can be inserted using a guide wire. In one example, the implant can be inserted over a guide wire. In another example, the implant can be delivered through a guide instrument.

The implant may further be augmented with a PMMA or CaP cement injection, other biologic agent, or an osteoconductive, osteoinductive and/or osteogenic agent. The augmentation material can be introduced through the implant, around the implant, and/or apart from the implant but at the affected bone region, such as into the lower region of a bone marrow lesion or below the lesion. For example, the implant can act as a portal to inject the augmentation material into the subchondral bone region.

While each of the above-mentioned treatment modalities can be administered independent of one another, it is contemplated that any combination of these modalities can be applied together and in any order so desired, depending on the severity or stage of development of the bone defect(s). Suitable implantable fixation devices for the surgical treatment of these altered bone regions or bone defects, especially at the subchondral level, are known. These devices and instruments can be used in combination with cements or hardening materials commonly used to repair damaged bone by their introduction into or near the site of damage, either to create a binding agent, cellular scaffold or mechanical scaffold for immobilization, regeneration or remodeling of the bone tissue. As previously stated, treatment of the bone defect at the subchondral level preferably is performed without disrupting the joint surface.

In a healthy joint such as a tibio-femoral joint, the compressive load between the contact bones (i.e., the femur and the tibia) is properly distributed, thus keeping the contact stresses in the cartilage to a reasonably low level. As the cartilage starts to wear out or degenerate locally, the tibio-femoral contact area reduces and starts to get localized at the site of the cartilage defect. The localization of the stresses may also occur due to varus or valgus deformity. Sometimes, the condition can occur because of osteoporosis, where bone becomes weak and is no longer able to support normal loads. This condition leads to higher localized contact stresses in the cartilage, and the subchondral region below the cartilage. Once the stresses reach beyond a certain threshold level, it leads to defects like bone marrow lesions and edema, and perhaps generates knee pain. If the problem persists, the high contact stresses can lead to sclerotic bone formation as well. The presence of sclerotic bone can compromise vascularization of the local area, and also create a mechanical mismatch in the bone tissue. This mismatch can start to expedite degeneration of all parts of the joint leading to increased levels of osteoarthritis.

Pain associated with osteoarthritic joints can be correlated to bone defects or changes at the subchondral level. In particular, bone defects such as bone marrow lesions, edema, fissures, fractures, etc. near the joint surface lead to abnormal stress distribution in the periarticular bone, which can cause inflammation and generate pain. By altering the makeup of the periarticular bone (which may or may not be sclerotic) in relation to the surrounding region, it is possible to change the structural integrity of the affected bone, leading to a resolution of the inflammation. Treatment of the bone in an effort to alter the structural makeup of the affected periarticular bone leads to reduced inflammation and pain has proven to be successful. Over time, restoration of normal physiologic stress distribution can be achieved in load bearing joints such as the hip and knee, and mechanical congruity restored, thereby resulting in healing of the inflammation and reduction or elimination of pain.

In general, the present disclosure provides examples related to instruments and associated methods for the surgical treatment of a joint, and particularly a bone defect at that joint region. More specifically, the examples relate to instruments for treating a bone defect of a joint at the subchondral level and associated methods. As previously mentioned, instruments and tools to carry out the SCP™ techniques mentioned above, such as pins, needles, cannulas, wires, etc. have been disclosed for treatment of subchondral defects in bone joints.

Previous instruments and methods generally utilize fluoroscopy to confirm accurate placement of devices used to carry out the SCP™. However, fluoroscopy provides a 2-dimensional image and requires the surgeon to extrapolate this infomraitn for application in 3-dimensions. Additionally, fluoroscopic equipment can be cumbersome to use and adds to the surgical needed to perform the SCP™. Further, fluoroscopy can also require a radiology technician to operate the equipment, which increase the cost of the procedure. Moreover, fluoroscopy exposes that patient, surgeon, and surgical team to a low, but measurable level of radiation.

The instruments and methods of the present disclosure simplify the procedure while improving the accuracy of a device delivered to a target area near the bone defect and eliminate or reduce the need for fluoroscopy assistance. The instruments and method of the present disclosure provide patient specific instruments that can improve the accuracy and precision of the SCP™.

In general, most surgeons can accurately locate by physical examination the position of a patient's patella, patella tendon, tibial tubercle, tibial crest, fibular head, medial malleolus, lateral malleolus, and ankle center. The instruments of the present disclosure incorporate patient specific surfaces that define a negative impression of one or more of a patient's anatomical landmarks or define a distance between two anatomical landmarks to aid in navigating to the target area near the subchondral defect.

Turning now to the drawings, FIG. 1 illustrates an exploded perspective view of an instrument 10 for navigating to a target area near a subchondral defect of a bone, in accordance with at least one example. The instrument can include a body portion 12 and a targeting device 18. The body portion 12 can have a front surface 14 and a patient specific surface 16 opposite the front surface 14. The patient specific surface 16 can define a negative impression of a portion of a skin surface of a patient. The negative impression of the portion of the skin surface can include an imprint of at least one of a first anatomical landmark and a second anatomical landmark. In an example, the first anatomical landmark can be a patella and the second anatomical landmark can be a tibial tubercle. The body portion 12 can have one or more visual markers 22, e.g., a MRI marker such as a metal or vitamin E. Additionally or alternatively, other visual markers can be used.

The body portion 12 can be formed over the skin surface of the patient and worn during an MRI. The body portion 12 can be attached to the patient in a position that can be replicated at a later date and/or by another surgeon. For example, in the example shown in FIG. 1, the body portion 12 can be placed on the patient's knee in the same position because the patient specific surface contours to the patient's skin surface and defines imprints of anatomical landmarks that are unique to the patient.

The one or more visual markers as well as the bone defect can show up in the MRI image. As discussed herein, this allows the surgeon to use the MRI to see where the bone defect is with respect to the body portion 12. At a later date, a surgeon can put the body portion 12 back on the patient—anchored to the anatomical landmarks—and use the targeting device 18 to target the bone defect by reading the MRI image identifying the visual marker and the bone defect. For example, the surgeon can secure the targeting device at the same level as the visual marker that most closely lined up with the bone defect during the MRI. In one example, the targeting device 18 can be coupled to the body portion 12 during the MRI, or, in the alternative, the targeting device 18 can be coupled to the body portion 12 after the MRI and during the SMP®.

The body portion 12 can be formed from a variety of moldable materials. For example, the body portion 12 can include, but is not limited to, plaster, fiberglass, silicone, epoxy, polyurethane foam, among others. In an example, the moldable materials can be applied to a patient and allowed to harden. In an example, the moldable material can include a pre-hardened material. The pre-hardened material can be moldable and can be applied to the patient. As pressure is applied, contact areas can deform to the contour of the skin surface of the patient including negative impressions of one or more anatomical landmarks. Thus, the moldable materials can include materials that are applied to a patient and allowed to harden and pre-hardened materials that are moldable, such that as pressure is applied, the pre-hardened material can conform to the patients skin surface.

The targeting device 18 can include a rail 21 and at least one device portal 20. The example shown in FIG. 1 includes a plurality of device portals 20. In an example, the rail 21 can be semi-circular or curved; however, it is understood that the rail 21 can be configured with any other shape having a variety of cross-sectional shapes. As shown in FIG. 1, the device portals 20 can be provided on the rail 21 for access to the target area. The device portals 20 can be configured to guide a device into a subchondral region of the bone for treatment at the target area. The device portals 20 can define a plurality of trajectories and are configured to provide accurate and controlled delivery of the device to the target area.

The targeting device 18 can be coupled to the front surface 14 of the body portion 12. In one example, the targeting device 18 can be releasably coupled to the body portion 12. For example, the targeting device 18 can include attachment member 19 that can be configured to engage with a corresponding slot 15 on the body portion 12. The body portion 12 can include a plurality of slots 15 positioned along the length of the body portion 12 to allow for varying vertical placement of the targeting device 18 along the body portion 12. Allowing for varying vertical placement can allow a surgeon to select a vertical height and device portal that can provide accurate delivery of a device to the target area in the subchondral bone. The body portion 12 having a surface contoured to a specific patient, the visual marker 22, and the targeting device 18 having at least one device portal 20 can allow a surgeon to accurately deliver a device to the target area in the subchondral bone of a patient.

In another example, the body portion 12 can be non-releasably coupled to the body portion 12. For example, either while the body portion 12 is being formed or after, the targeting device 18 can be non-releasably coupled to the body portion 12 via any suitable connection means including, but not limited to, fasteners (such as rivets), welding, an adhesive, or the like. Example adhesives can include, but are not limited to, epoxy, silicone, Velcro, magnets, and coband, among others.

In one example, the rail 21 can be coupled to the body portion 12 and extend at an angle to a transverse plane of a tibia. The angle could be in the range of about 1 to about 15 degrees, such as about 2 to about 10 degrees, e.g., 3 degrees, 4 degree, 5 degrees, 6 degrees, 7 degrees, 8 degrees, and 9 degrees. In one example, the rail 21 can be configured to extend at an angle of about 7 degrees to a transverse plane of a tibial plateau. This slight angle can enable the rail 21 to be oriented parallel to the tibial plateau (which typically has a natural, inherent slope), thereby allowing the user to have instrumentation that better matches the natural contours of the bone to be treated and which allows for the correct angular access to the target area. Accordingly, the angular orientation of the rail 21 allows the user a greater angular opening to access the bone clear of ligament and other surrounding soft tissue, and prevents inadvertent angular insertion of any instruments or devices through cartilage or other unintended bone or soft tissue, causing damage to the joint.

Figure 2:
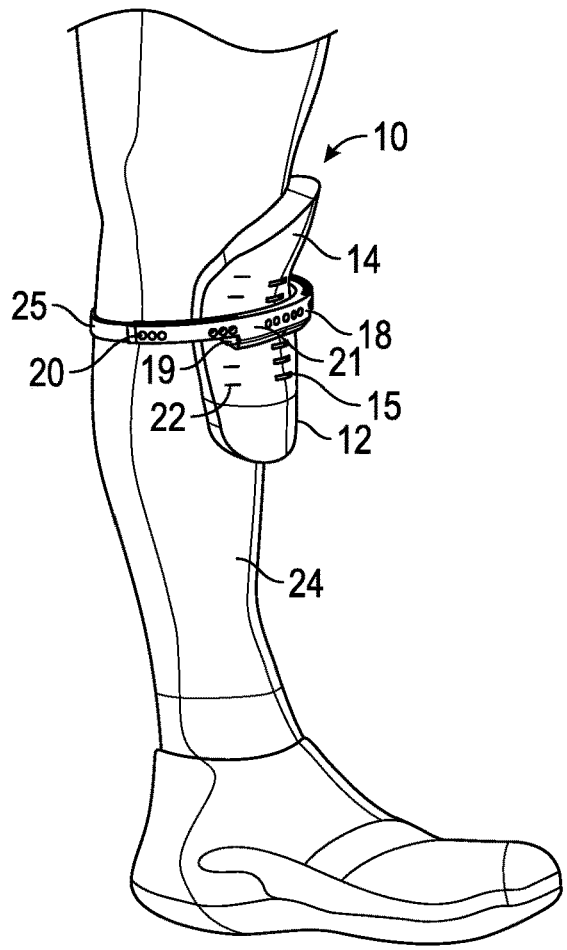
FIG. 2 illustrates a perspective view of the instrument in FIG. 1 positioned on a patient, in accordance with at least one example.

FIG. 2 illustrates a perspective view of the instrument 10 in FIG. 1 positioned on a patient 24, in accordance with at least one example. As shown in FIG. 2, the body portion 12 is seated on the patient 24 and covering the patella and the tibial tubercle. Since the body portion 12 has the patient specific surface 16 (shown in FIG. 1), the body portion 12 can be placed in substantially the same place as when the MRI image was taken prior to surgery. The targeting device 18 can be coupled to the body portion 12, as discussed herein. In addition to or in the alternative, the targeting device 18 can include a strap 25 that can couple or further secure the targeting device 18 to the body portion 12.

Figure 3:
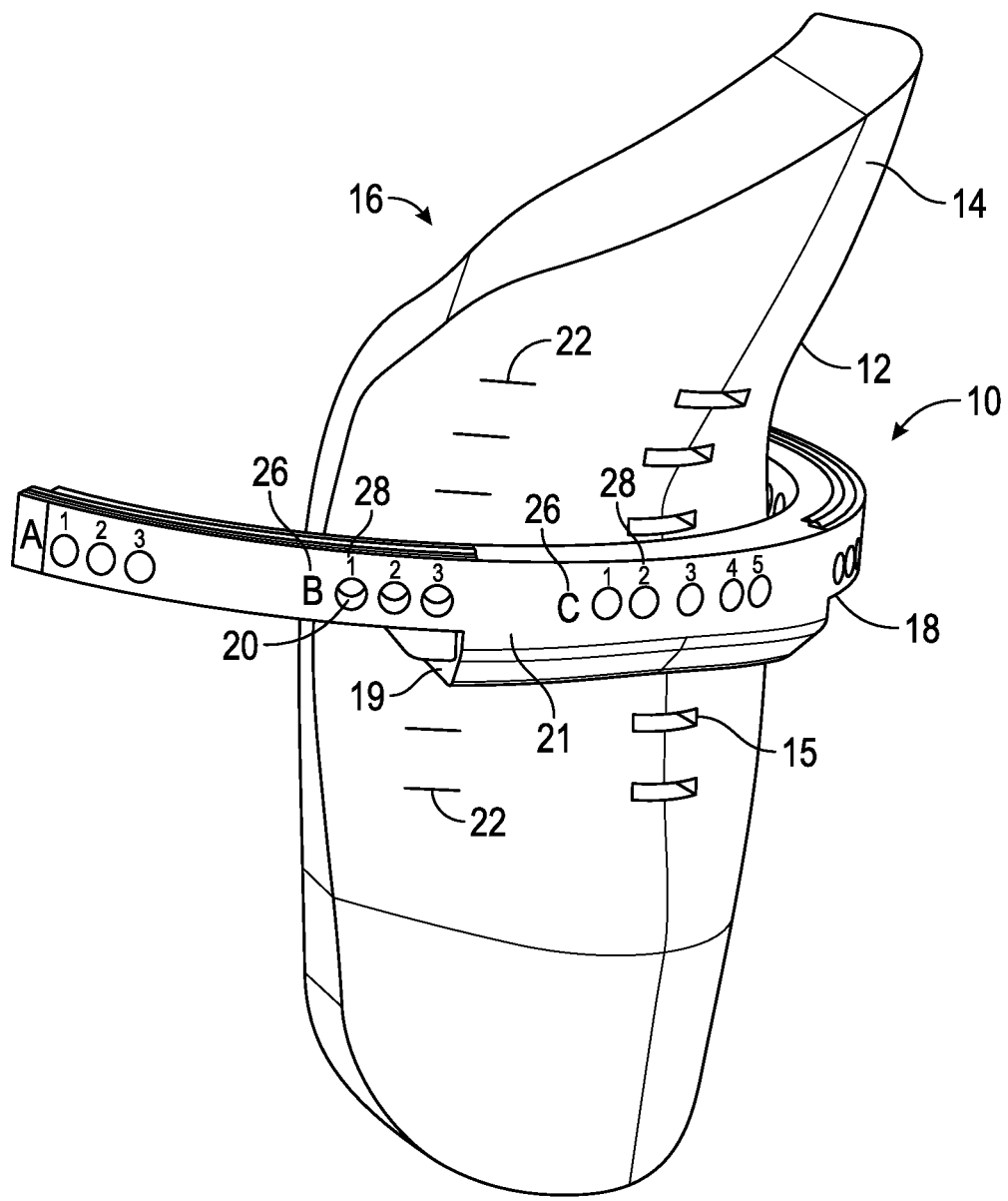
FIG. 3 illustrates close-up view of the instrument in FIG. 1, in accordance with at least one example.

FIG. 3 illustrates a close-up view of the instrument 10 in FIG. 1, in accordance with at least one example. As shown in FIG. 3, the rail 21 can include markings 26 and 28 that can be used by a surgeon to identify a device portal that can be used to access the target area. For example, markings 26 can be letter markings and markings 28 can be numerical markings. The markings 26 and 28 can assist the surgeon during surgery and/or during the MRI in identifying a particular device portal 20 to access the target area. In an example, the markings can identify the device portals 20 by a letter marking and a numerical marking such as "A1."

Figure 4A:
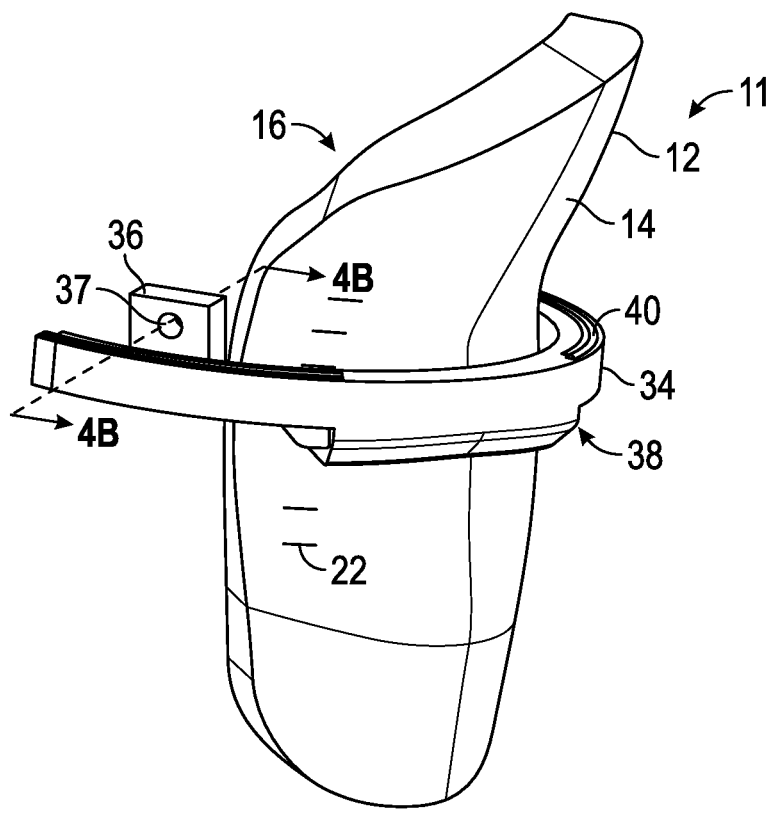
FIG. 4A illustrates a perspective view of an instrument for navigating to a target area near a subchondral defect of a bone, in accordance with at least one example.
Figure 4B:
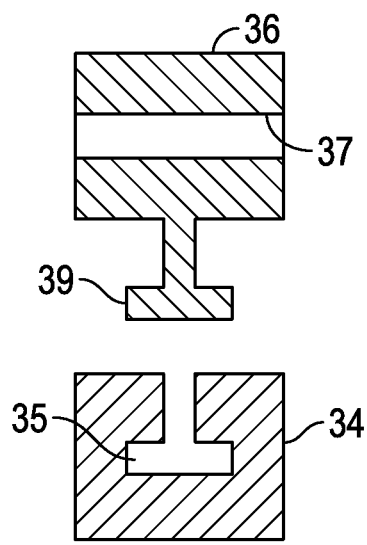
FIG. 4B illustrates a cross-sectional view along cut line 4B-4B in FIG. 4A.

FIG. 4A illustrates a perspective view of an instrument 11 for navigating to a target area near a subchondral defect of a bone, in accordance with at least one example. The instrument in FIG. 4A can include the body portion 12 as shown in FIG. 1 and a targeting device 38. The targeting device 38 can be coupled to the body portion 12 and include a rail 34. The rail 34 can further include a slot 40 and an alignment guide 36 including at least one device portal 37. The alignment guide 36 is attachable to the rail 34. In an example, the alignment guide 36 is detachably coupled to the rail 34 and moveable along a length of the rail 34. FIG. 4B illustrates a cross-sectional view along cut line 4B-4B in FIG. 4A. As shown in FIG. 4B, the rail 34 can define the slot 40 (e.g., a T-slot) extending along the length of the rail 34. The alignment guide 36 can define a corresponding T-projection 39 that fits into the slot 40 on the rail 34. The alignment guide 36 and/or the rail 34 can include a locking member that can secure the alignment guide 36 to the rail 34 at a predetermined location. The device portal 37 of the alignment guide 36 can be patient specific. For example, the device portal 37 can be formed in the alignment guide 36 having a trajectory previously determined by, for example, a surgeon based on a patient's MRI imaging data.

Figure 5:
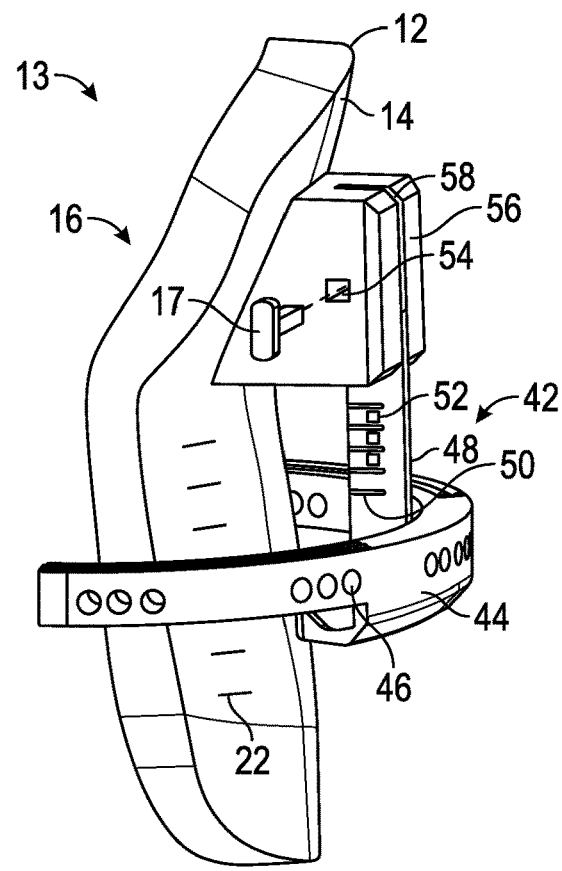
FIG. 5 illustrates a perspective view of an instrument for navigating to a target area near a subchondral defect of a bone, in accordance with at least one example.

FIG. 5 illustrates a perspective view of an instrument 13 for navigating to a target area near a subchondral defect of a bone, in accordance with at least one example. The instrument 13 of FIG. 5 can include the body portion 12 as shown in FIG. 1, an attachment block 56, and a targeting device 48. As discussed herein, the body portion 12 can include a front surface 14 and a patient specific surface 16 opposite the front surface 14. The patient specific surface 16 can define a negative impression of a portion of a skin surface of a patient. The negative impression of the portion of the skin surface can include an imprint of at least one of a first anatomical landmark and a second anatomical landmark. In the example in FIG. 5, the negative impression includes an imprint of both the first anatomical landmark and the second anatomical landmark. In an example, the first anatomical landmark can be a patella and the second anatomical landmark can be a tibial tubercle.

The attachment block 56 can be attachable to the front surface 14 of the body portion 12. The attachment block 56 can be detachably coupled to the targeting device 42. In an example, the attachment block 56 can define a slot 58 extending along a length of the attachment block 58. The attachment block 56 can also define an aperture 54 extending through the width of the attachment block 56. The aperture 54 can be configured to receive a locking pin 17 to lock the vertical position of the targeting device 42 along the body portion 12. Other attachment mechanism between the attachment block 58 and the targeting device 42 can be used.

The targeting device 42 can include a rail 44. The rail 44 can be the same as either one of the rails illustrated in FIGS. 1 and 4A. As shown in FIG. 5, the rail 44 can include a plurality of device portals 46. The targeting device 42 in FIG. 5 can further include an elongate portion 48 extending from the rail 44. The elongate portion 48 can be positioned and moveable within the slot 58 of the attachment block 58. The elongate portion 48 can include a plurality of markings 50 and a plurality of apertures 52. The markings 50 can aid the user when adjusting the vertical position of the target device 42 along the body portion 12. In an example, the body portion 12 can be placed on a patient during an MRI. The surgeon can note which visual marker aligns most closely with the bone defect. Thus, after the MRI and during the SMP™, the surgeon can place the body portion 12 back onto the patient at the same location and couple the targeting device 42 to the body portion 12. The surgeon can then adjust the vertical position of the targeting device 42 such that the rail 44 substantially aligns with the visual marker 50 previously noted by the surgeon. In another example, the targeting device 42 can be coupled to and vertically adjusted along the body portion 12 during the MRI.

The apertures 52 in the elongate portion 48 can interact with the locking pin 17 to lock the rail 44 at a fixed vertical position with respect to the body portion 12. For example, the locking pin can extend through the aperture 54 in the attachment block 56, through an aperture 52 in the elongate portion 48, and into a corresponding aperture in the opposing side of the attachment block 56.

Figure 6:
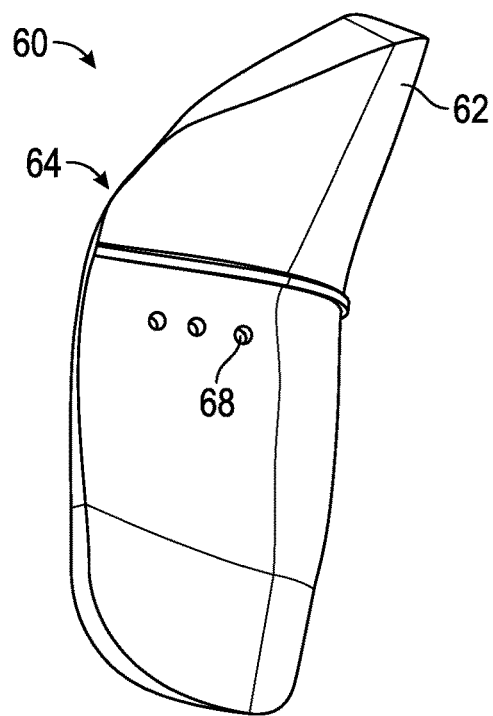
FIG. 6 illustrates a perspective view of an instrument for navigating to a target area near a subchondral defect of a bone, in accordance with at least one example.

FIG. 6 illustrates a perspective view of an instrument 60 for navigating to a target area near a subchondral defect of a bone, in accordance with at least one example. The instrument 60 can include a body portion 60 having a front surface 62 and a patient specific surface 64 opposite the front surface 62. The patient specific surface 64 can define a negative impression of a portion of a skin surface of a patient. For example, the negative impression of the portion of the skin surface can include an imprint of at least one of a first anatomical landmark and a second anatomical landmark. In an example, the first anatomical landmark can be the patella and the second anatomical landmark can be the tibial tubercle. The instrument 60 can further include a plurality of device portals 68 extending from the front surface 62 to the patient specific surface 64.

During an MRI, the body portion 60 can be formed on the patient and the surgeon can mark locations on the body portion 60 that align with the defect. After the MRI, the marked locations can be drilled out to form the device portals 68 such that during surgery, the surgeon can simply reattach the body portion 60 and the device portals 68 will be aligned with the defect.

In an example, a method of accessing a target area near a defect in a bone can include positioning a molded cast on a patient. For example, the molded cast can be body portion 12 as shown in FIGS. 1-5 or body portion 60 shown in FIG. 6. The molded cast can have a front surface and a patient specific surface. The patient specific can define a negative impression of a skin surface of the patient, where the negative impression includes an imprint of at least one anatomical landmark. Further, the body portion can include a visual marker, e.g., a MRI marker. The method can include selecting, based on a magnetic resonance imaging (MRI) image identifying the visual marker and the defect, a device portal from a plurality of device portals located on a targeting device to access the target area. The method can include accessing the target site with a device via the selected device portal, where accessing the target area can include creating an access path to the target area. The method can further include injecting an injectable material into the subchondral bone via the access path for reinforcing the subchondral bone.

As discussed herein, the molded cast (also referred to herein as "body portion") can be formed on the patient before/during an MRI. The body portion can be formed onto the knee in a position that can be replicated by another surgeon at a later date. This is accomplished by forming the body cast over palpable anatomical landmarks such as the patella and tibial tubercle. However, other anatomical landmarks can be used. The visual marker that most closely aligns with the bone defect can be recorded to assist others during surgery to align the device portals with the bone defect. For example, during surgery the targeting device including a plurality of device portals can be positioned such that at least one of the plurality of device portals align with the visual marker recorded.

The method can include forming the molded cast on the patient such that the molded cast extends over the skin surface including at least one anatomical landmark. In an example, the molded cast extends over the skin surface including two anatomical landmarks. The method can include identifying the subchondral defect in the bone of the patient under magnetic resonance imagining (MRI). The method can include coupling, while under MRI imagining, a MRI marker to the cast to provide a reference point on the molded cast in relation to the subchondral defect of the bone. Forming the molded cast on the patient can include applying a moldable material to the skin surface of the patient including the at least one anatomical landmark, and allowing the moldable material to harden.

Figure 7:
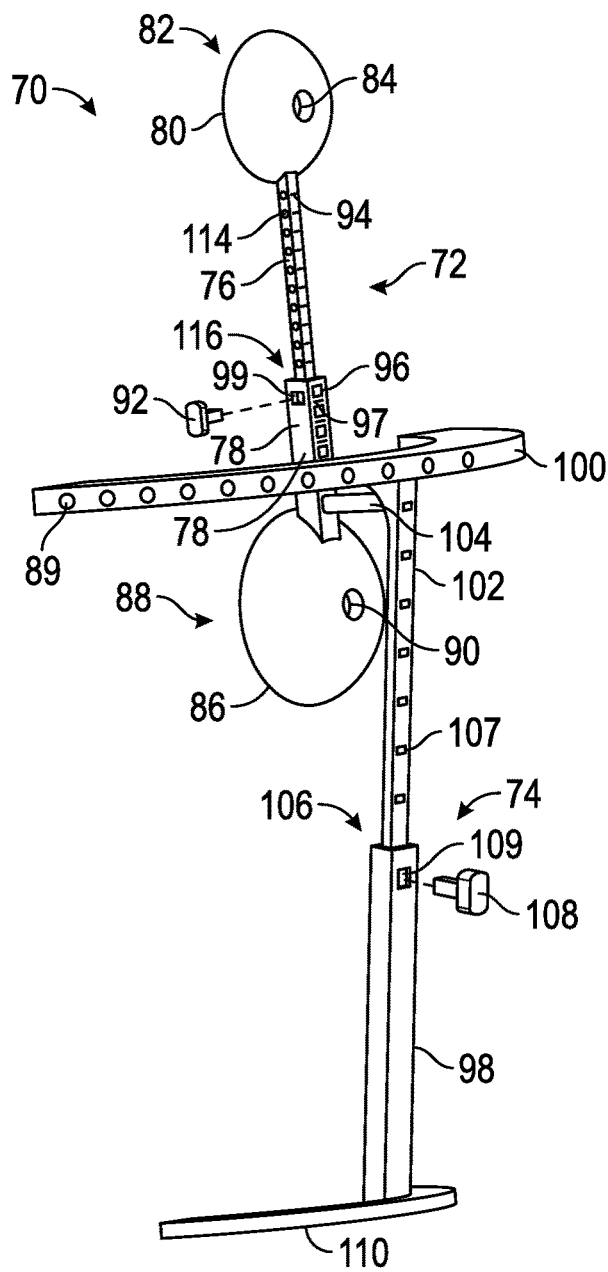
FIG. 7 illustrates a perspective view of an instrument for navigating to a target area near a subchondral defect of a bone, in accordance with at least one example.

FIG. 7 illustrates a perspective view of an instrument 70 for navigating to a target area near a subchondral defect of a bone, in accordance with at least one example. The instrument 70 can include a reference guide 72 and a targeting device 74 configured to couple to the reference guide 72. The reference guide 72 can include a first portion 82 and a second portion 88. The first and second portions 82, 88 can be moveable with respect to each other. The first portion 82 can include a first contact pad 80 configured to be aligned with a first anatomical landmark. That is, the first contact pad 80 can have a first contact surface that is configured to be seated on the first anatomical landmark. The second portion 88 can include a second contact pad 86 that is configured to be aligned with a second anatomical landmark. That is, the second contact pad 86 can have a second contact surface that is configured to be seated on the second anatomical landmark. While there are various palpable anatomical landmarks that can be used, in one example, the first anatomical landmark can be a patella and the second anatomical landmark can be a tibia tubercle. Other examples include, but are not limited to, a patella tendon, a fibular head, a tibial crest, and a quadriceps muscle.

In an example, the first portion 82 can include a first elongate body 76 extending from the first contact pad 80. The first elongate body 76 can include a plurality of apertures 114 configured to receive a locking pin 92 to lock the first portion 82 with respect to the second portion 88. The elongate body 76 can include a plurality of visual markings 94 that can be used to indicate a distance between the first contact pad 80 and the second contact pad 86.

The second portion 88 can include a second elongate body 78 extending from the second contact pad 86. The second elongate body 78 can define a bore 116 that slidingly receives the first elongate body 76 such that the first portion 82 and the second portion 88 are moveable with respect to each other. The elongate body 78 can define a bore 99 extending through the width and configured to receive a locking pin 92 that can extend through one of the apertures 114 in the first elongate body 76. For example, the bore 99 can align with the aperture 114 and the locking pin 92 can be inserted through both the bore 99 and the aperture 114.

As discussed herein, the reference guide 72 can be placed on a patient before/during an MRI such that the first contact pad 80 contours to the patient's first anatomical landmark (e.g., patella) and the second contact pad 86 contours to the patient's second anatomical landmark (e.g., tibial tubercle). The distance apart between the first contact pad 80 and the second contact pad 86 can be indicated by the calibrated marks (e.g., markings 94). The markings 94 can allow the placement of the reference guide 72 to be easily replicated subsequently by re-extending the reference guide 72 to the recorded, calibrated, mark. Thus, the reference guide 72 can be placed onto the individual patient's body at the same location as when the MRI image was taken. As seen in FIG. 7 the first and second contact pads 80, 86 can include apertures 84 and 90, respectively. When the reference guide 72 is first attached to a patient, the patient's skin exposed through the apertures 84, 90 can be marked, e.g., with a stitch, marker, or temporary tattoo such that the placement of the first and second contact pads 80, 86 during the surgery will be more accurate.

In an example, the second elongate body 78 can include a plurality of apertures 96 and a plurality of markers 97. The markers 97 can be MRI markers such as metal and/or Vitamin E. The apertures 96 can be configured to receive a projection 10 of the targeting device 74 to couple the targeting device 74 to the reference guide 72, as discussed herein. Each marker 97 can be associated with an aperture such that during the MRI, the surgeon can record the marker 97 that most closely aligns with the bone defect. Therefore, subsequently, the targeting device 74 can be attached to the reference guide 72 at the recorded position along the second elongate body 78.

The targeting device 74 can be attachable to the reference guide 72. The targeting device 74 can include a rail 100 and at least one device portal 89 configured to guide a device into a subchondral region of the bone for treatment at the target area. As shown in the example of FIG. 7, the at least one device portal 89 can include a plurality of device portals 89 provided on the rail 100 for access to the target area. In other examples, at least one device portal can be provided on an alignment guide that is attachable to the rail, as will be discussed in further detail below.

The targeting device 74 can include a main body 102 and a base portion 98. The main body 102 can extend from the rail 100 and have a plurality of apertures 107. The base portion 98 can define a bore 106 that receives the main body 102, the base portion 98 terminating at a support portion 110. In use, the base 110 can be seated against the center of the ankle. In another example, the base 110 can be seated against the tibial crest. The base portion 98 can include an aperture 109 in a side wall of the base portion 98. The aperture 109 and one of the apertures 107 on the main body 102 can align and receive a locking pin 108 to restrict movement between the main body 102 and the base portion 98.

Figure 8:
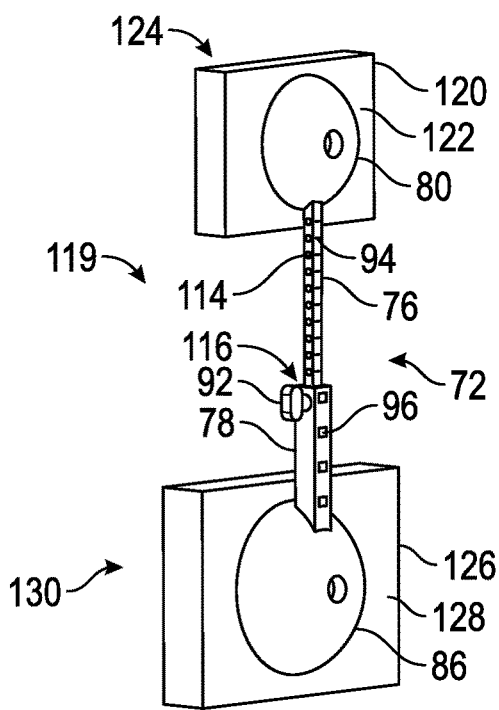
FIG. 8 illustrates a perspective view of a reference guide, in accordance with at least one example.

FIG. 8 illustrates a perspective view of a reference guide 119, in accordance with at least one example. The reference guide 119 can include the reference guide 72 as described in FIG. 7, and can further include a first molded portion 120 coupled to the first contact pad 80 and a second molded portion 126 coupled to the second contact pad 86. The first molded portion 120 can include a front surface 122 and a first patient specific surface 124 opposite the front surface 122. The front surface 122 can be coupled to the first contact pad 80 and the first patient specific surface 124 can have a contour of a first anatomical landmark of a patient. That is, the first patient specific surface 124 can be a negative impression of the first anatomical landmark, such as a patella. The second molded portion 126 can include a front surface 128 and a first patient specific surface 130 opposite the front surface 128. The front surface 128 can be coupled to the second contact pad 86 and the second patient specific surface 130 can have a contour of a second anatomical landmark of the patient. That is, the second patient specific surface 130 can be a negative impression of the second anatomical landmark, such as a tibial tubercle. The first and second molded portions 120, 126 can be used to provide secure contact between the reference guide 119 and the patient. The reference guide 119 can be used with the targeting device 74 in FIG. 7 or the targeting device 75 discussed hereafter in FIG. 9.

Figure 9:
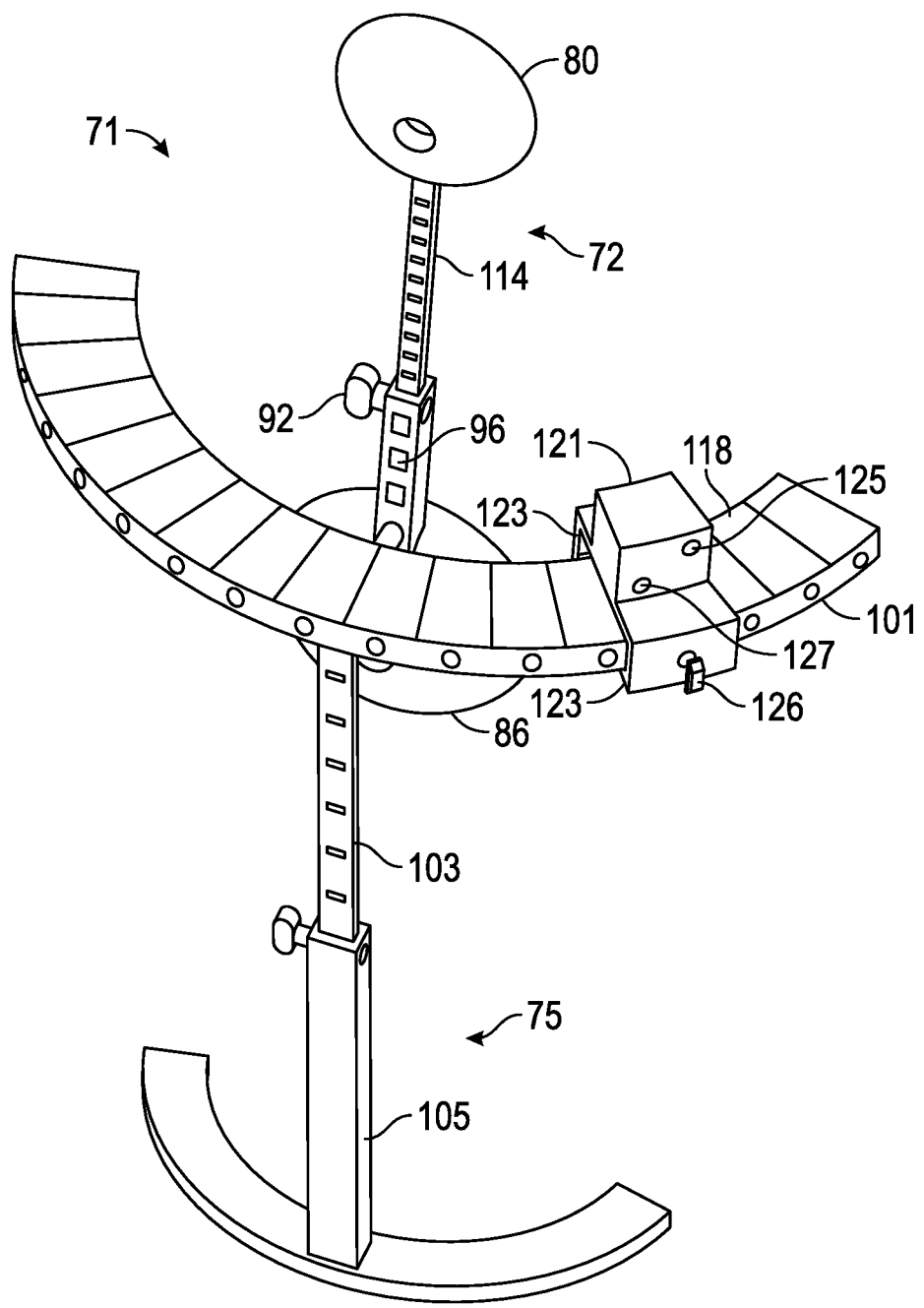
FIG. 9 illustrates a perspective view of an instrument for navigating to a target area near a subchondral defect of a bone, in accordance with at least one example.

FIG. 9 illustrates a perspective view of an instrument 71 for navigating to a target area near a subchondral defect of a bone, in accordance with at least one example. The instrument 71 in FIG. 9 can include the reference guide 72 as discussed in FIG. 7 and a targeting guide 75. The targeting guide 75 can be coupled to the reference guide 72 as discussed herein. The targeting guide 75 in FIG. 9 can include a rail 101, a main body 103 extending from the rail 101, and an alignment guide 121 including at least one device portal (e.g., device portals 125, 127). The targeting guide 75 can include a base portion 105 that is configured to receive a portion of the main body 103.

The alignment guide 121 can be attachable to the rail 101 such that the alignment guide 121 can move along the length of the rail 101. The rail 101 can include a calibrated surface 118 such that a surgeon can determine where to place the alignment guide 121 for accurate and controlled delivery of a device to the target area. The alignment guide 121 can include a tightening pin 126 that can rotate and secure the alignment guide 121 at a desired location along the rail 101. In an example, the alignment guide 121 can include a pair of hinged arms 123 that extend partially over the rail 101. As discussed herein, the device portals 125, 127 can be patient specific or general device portals. For example, the device portals 125, 127 can be formed in the alignment guide 121 having a trajectory previously determined by, for example, a surgeon based on a patient's MRI imaging data.

Figure 10:
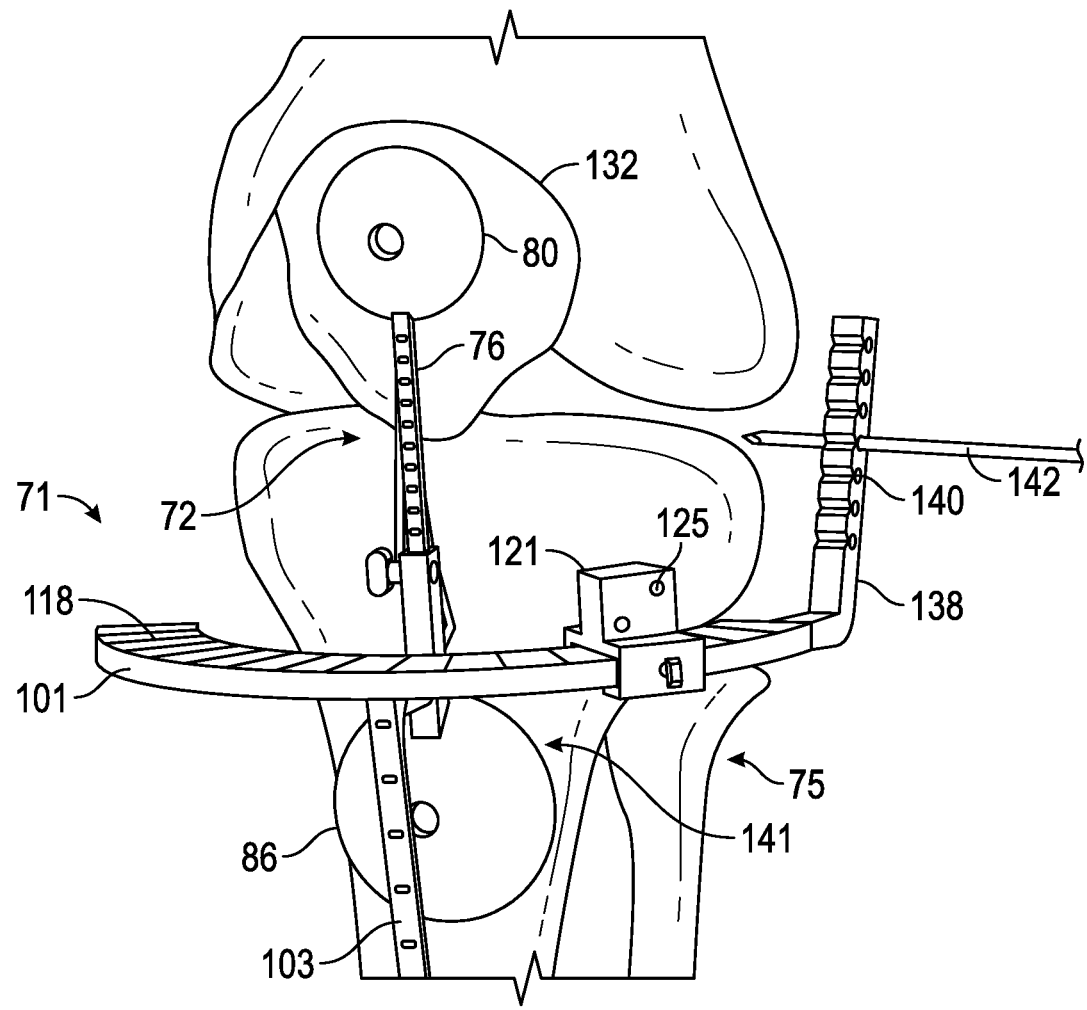
FIG. 10 illustrates perspective view of the instrument of FIG. 9 coupled to a patient, in accordance with at least one example.

FIG. 10 illustrates a perspective view of the instrument 71 coupled to a patient, in accordance with at least one example. The instrument 71 includes the reference guide 72 and the targeting device 75. As shown in FIG. 10, the first contact pad 80 can be aligned with the patella 132 and the second contact pad 86 can be aligned with the tibial tubercle 141. The targeting device 75 in FIG. 10 can also include a joint line guide 138 including apertures 140. The joint line guide 138 can be attached to the rail 101 and configured to receive a needle 142. For example, after SCP™, a joint line can be confirmed by inserting the needle into the joint. Confirming the joint line can be used to confirm that the SCP™ did not disturb the articulation surface.

In an example, a method of accessing a target area near a defect in a bone can include positioning a reference guide on a patient, the reference guide including a first portion and a second portion. The first portion can include a first contact pad configured to be placed on a first anatomical landmark of the patient and the second portion can include a second contact pad configured to be placed on a second anatomical landmark of the patient. As discussed herein, the reference guide can include a plurality of visual markers.

The method can include determining, based on an MRI image identifying the plurality of visual markers and the defect, a coupling location corresponding to one visual marker of the plurality of visual markers and coupling a target device to the reference guide at the coupling location. The target device can have a least one device portal configured to guide a device into a subchondral region of the bone for treatment at the target site. The method can include accessing the target site with a device via the selected device portal. The method can include determining, based on the MRI image, which device portal of the plurality of device portals is best suited to access the target site. Further, the method can include determining, based on the MRI image, a location along the rail to position the alignment guide to access the target site.

In an example, the reference guide can include a first contact pad coupled to a first molded portion and a second contact pad coupled to a second molded portion, where the first molded portion has a first patient specific surface configured to contact a first anatomical landmark of a patient, and the second molded portion has a second patient specific surface configured to contact a second anatomical landmark of the patient. In that example, the method can include forming the first molded portion and the second molded portion. Forming the first molded portion and the second molded portion can include applying a moldable material on the patient at the first anatomical landmark, coupling the first contact pad to the moldable material, applying the moldable material on the patient at the second anatomical landmark, coupling the second contact pad to the moldable material, and allowing the moldable material to harden. The method can include accessing the target site by creating an access path to the target site and injecting an injectable material into the subchondral bone via the access path for reinforcing the subchondral bone.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An instrument for navigating to a target area near a subchondral defect of a bone, comprising: a body portion having a front surface and a patient specific surface opposite the front surface, the patient specific surface defining a negative impression of a portion of a skin surface of a patient, and a targeting device configured to be attached to the front surface of the body portion, the targeting device including a rail and at least one device portal configured to guide a device into a subchondral region of the bone for treatment at the target area, wherein the negative impression includes an imprint of at least one anatomical landmark, wherein the at least one anatomical landmark includes first and second anatomical landmarks, wherein the first anatomical landmark is a patella and the second anatomical landmark is a tibial tubercle.

2. The instrument of claim 1, wherein the body portion includes a magnetic resonance image marker.

3. The instrument of claim 1, wherein the targeting device is releasably coupled to the body portion.

4. The instrument of claim 1, wherein the targeting device is non-releasably coupled to the body portion.

5. The instrument of claim 1, wherein the at least one device portal defines a trajectory and is configured to provide accurate and controlled delivery of the device to the target area.

6. The instrument of claim 1, wherein the at least one device portal is provided on the rail for access to the target area.

7. The instrument of claim 1, wherein the at least one device portal is provided on an alignment guide attachable to the rail, the alignment guide being detachable and movable along a length of the rail.

8. The instrument of claim 1, wherein the body portion is formed from at least one of plaster, fiberglass, silicone, epoxy, and polyurethane foam.

9. An instrument for navigating to a target area near a subchondral defect of a bone, comprising: a body portion having a front surface and a patient specific surface opposite the front surface, the patient specific surface defining a negative impression of a portion of a skin surface of a patient, an attachment block attachable to the front surface of the body portion; and a targeting device, the targeting device including: a rail; an elongate portion extending from the rail, the elongate portion attachable to and moveable relative to the attachment block; and at least one device portal configured to guide a device into a subchondral region of the bone for treatment at the target area, wherein the at least one anatomical landmark includes first and second anatomical landmarks, wherein the first anatomical landmark is a patella and the second anatomical landmark is a tibia! tubercle.

10. The instrument of claim 9, wherein the negative impression includes an imprint of at least one anatomical landmark.

11. The instrument of claim 9, wherein the body portion includes a visual marker.

12. The instrument of claim 9, wherein the at least one device portal is provided on the rail for access to the target area.

13. The instrument of claim 9, wherein the at least one device portal is provided on an alignment guide attachable to the rail, the alignment guide being detachable and movable along the length of the rail.

* * * * *

UNITED STATES PATENT AND TRADEMARK OFFICE
CERTIFICATE OF CORRECTION

PATENT NO. : 10,561,442 B2  
APPLICATION NO. : 15/527449  
DATED : February 18, 2020  
INVENTOR(S) : Hanson et al.

Page 1 of 1

It is certified that error appears in the above-identified patent and that said Letters Patent is hereby corrected as shown below:

On the Title Page

On page 2, in Column 1, item (56) under "Other Publications", Line 5, delete "15805371.6," and insert --15805373.6,-- therefor On page 2, in Column 1, item (56) under "Other Publications", Line 7, delete "15805371.6," and insert --15805373.6,-- therefor On page 2, in Column 1, item (56) under "Other Publications", Line 9, delete "15805371.6," and insert --15805373.6,-- therefor In the Claims In Column 20, Line 10, in Claim 1, after "comprising:", insert --¶--

In Column 20, Line 45, in Claim 9, after "comprising:", insert --¶--

In Column 20, Line 50, in Claim 9, after "and", insert --¶--

In Column 20, Line 51, in Claim 9, after "including:", insert --¶--

In Column 20, Line 51, in Claim 9, after "rail;", insert --¶--

In Column 20, Line 53, in Claim 9, after "and", insert --¶--

Signed and Sealed this  
Sixth Day of April, 2021

Drew Hirshfeld  
*Performing the Functions and Duties of the*  
*Under Secretary of Commerce for Intellectual Property and*  
*Director of the United States Patent and Trademark Office*